United States Patent [19]
Aboutalib et al.

[11] Patent Number: 5,859,686
[45] Date of Patent: Jan. 12, 1999

[54] EYE FINDING AND TRACKING SYSTEM

[75] Inventors: Omar Aboutalib, Diamond Bar; Richard Roy Ramroth, Long Beach, both of Calif.

[73] Assignee: Northrop Grumman Corporation, Los Angeles, Calif.

[21] Appl. No.: 858,841

[22] Filed: May 19, 1997

[51] Int. Cl.$^6$ ................... A61B 3/14; A61B 3/10; A61B 3/00
[52] U.S. Cl. ................ 351/209; 351/221; 351/246
[58] Field of Search .................... 351/221, 211, 351/205, 212, 206, 246, 247, 210, 209

[56] References Cited

U.S. PATENT DOCUMENTS

| | | |
|---|---|---|
| 3,462,604 | 8/1969 | Mason . |
| 5,093,567 | 3/1992 | Staveley . |
| 5,106,184 | 4/1992 | Milbocker . |
| 5,196,873 | 3/1993 | Yamanobe et al. . |
| 5,218,387 | 6/1993 | Ueno et al. . |
| 5,231,674 | 7/1993 | Cleveland et al. . |

*Primary Examiner*—Hung X. Dang
*Attorney, Agent, or Firm*—Terry J. Anderson; Karl J. Hoch, Jr.

[57] ABSTRACT

A system and method for finding and tracking the location of a subject's eyes. This system and method employs an imaging apparatus which produces digital image frames including the face and eyes of a subject. An eye position finding and tracking apparatus is also included to average the intensity representing pixel values within respective $M_x$ by $M_y$ pixel blocks of a digitized image frame to create elements of output matrices. Then, elements of the output matrices are compared to various threshold values. These threshold values are chosen so as to identify which matrix elements correspond to a $M_x$ by $M_y$ pixel block potentially representing an image of the subject's pupil and at least the portion of the subject's iris (i.e. a potential eye location). Once the flagged matrix elements have been determined, any $M_x$ by $M_y$ pixel block corresponding to a flagged matrix element can be designated as an actual subject eye location. However, it is preferred that further steps be taken to confirm the actual eye location, as well as to track the changing position of the subject's eye. Accordingly, the preferred system and method include a provision for tracking the location of a center of each $M_x$ by $M_y$ pixel block representing a potential eye location in each subsequent image frame produced from the imaging apparatus. Further, a provision is included to detect a blink at the location. Such a blink confirms the potential eye location is an actual eye location.

42 Claims, 10 Drawing Sheets

EYE FINDING AND TRACKING SYSTEM

BACKGROUND

1. Technical Field:

This invention relates to a system and method for finding and tracking the location of a subject's eyes.

2. Background Art:

Eye finding and tracking devices are employed for many purposes. For example, such devices are often used in vehicle operator drowsiness and intoxication detection systems. When a person is responsible for operating a vehicle, such as an automobile, it is critical that the person be capable of demonstrating basic cognitive and motor skills that will assure the safe operation of the vehicle. Lack of sleep, boredom or consumption of drugs or alcohol can impair a vehicle operator's ability to safely operate the vehicle. Therefore, it is important when designing an impaired driver detection system to continuously evaluate an operator's ability to control the vehicle. Impaired driver detection systems are useful because they avoid or reduce personal injury and property damage by preventing accidents.

An example of a known apparatus for eye finding and tracking which is employed in a vehicle operator drowsiness detection system employs two images of a driver's face. One of the images is obtained by illuminating the driver's face from a first direction, and the other is obtained by illuminating the driver's face from another direction. The two images are processed to detect three-dimensional positions of the driver's eyes. In another, example of a known eye finding and tracking system, an image of a vehicle driver's head is processed to determine the widest portion of the driver's face. From this determination, calculations are performed based on an analysis of the image and assumed geometric relationships of the eyes to the widest portion of the operator's face to define two rectangular regions which should include the operator's eyes.

Eye finding and tracking devices are also useful for other applications. For instance, these devices can be employed in systems designed to monitor the attentiveness of a machine operator, or a person working at a control console such as an air traffic controller. Another example where eye finding and tracking can be useful is in conjunction with an identification system which employs iris pattern matching techniques.

Although systems employing current eye finding and tracking devices work reasonably well for their intended purpose, it is a primary object of the present invention to provide an improved eye finding and tracking system which can determine the location of a subject's eyes within an image of his or her face and thereafter track the changing locations of the subject's eyes in subsequent images with greater accuracy than has been achieved in the past.

SUMMARY

The above-described objectives are realized with embodiments of the present invention directed to a system and method for finding and tracking the location of a subject's eyes. The system and method employ an imaging apparatus which produces digital image frames including the face and eyes of a subject. Each digital image frame comprising an array of pixel values representing the intensity of light reflected from the face of the subject. These intensity representing pixel values are located at positions in the array specified by x and y coordinates. An eye position finding and tracking apparatus is used to average the intensity representing pixel values within respective $M_x$ by $M_y$ pixel blocks of a digitized image frame to create elements of plural output matrices. Then, elements of the output matrices are compared to various threshold values. These threshold values are chosen so as to identify which matrix elements correspond to a $M_x$ by $M_y$ pixel block which includes pixel values potentially representing an image of the subject's pupil and at least the portion of the subject's iris.

Specifically, the aforementioned averaging process involves respectively averaging the intensity representing pixel values within three vertically arranged $M_x$ by $M_y$ pixel blocks in the upper left-hand corner of a first digitized image frame to create a first three-element column of a first output matrix. Next, the intensity representing pixel values within three vertically arranged $M_x$ by $M_y$ pixel blocks, each of which is offset to the right by one column of the array in relation to the last averaged pixel block, are respectively averaged to create a new column of the first output matrix. This last step is repeated until the three vertically arranged $M_x$ by $M_y$ pixel blocks which include pixel values from the last column of the array have been averaged to create a last column of the output matrix. The intensity representing pixel values within three more vertically arranged $M_x$ by $M_y$ pixel blocks are then respectively averaged starting at a position on the left-hand side of the array which is offset downward by one row in relation to a previously averaged pixel blocks. This averaging creates a first three-element column of a new output matrix. Next, the intensity representing pixel values within three vertically arranged $M_x$ by $M_y$ pixel blocks each of which is offset to the right by one column of the array in relation to a last averaged pixel blocks are respectively averaged to create a new column of the new output matrix. This step is then repeated until the three vertically arranged $M_x$ by $M_y$ pixel blocks which include pixel values from the last column of the array have been averaged to create a last column of the new output matrix. Finally, the above-described process of averaging pixel blocks which are offset downward by one row is continued the until the three vertically arranged $M_x$ by $M_y$ pixel blocks which include pixel values from the last column and row of the array have been averaged to create a last column of a last output matrix.

The specifics of the aforementioned comparing process includes comparing each element of each output matrix to a threshold range. The threshold range has a lower limit representing the lowest expected average of the intensity representing pixel values within a $M_x$ by $M_y$ pixel block corresponding to an image of the subject's pupil and at least a portion of the subject's iris for the particular illumination condition present at the time the image was produced. Similarly, the upper limit of the threshold range represents the highest expected average of the intensity representing pixel values within the $M_x$ by $M_y$ pixel block corresponding to the image of the subject's pupil and at least the portion of the subject's iris for the particular illumination condition present at the time the image was produced. Once the threshold range has been employed, any output matrix element which both exceeds a lower limit of the threshold range and is less than an upper limit of the threshold range is flagged. Next, threshold values are compared to the average of the intensity representing pixel values within each $M_x$ by $M_y$ pixel block immediately surrounding any pixel block corresponding to a flagged output matrix element. Any previously flagged output matrix element which has any surrounding pixel block which fails to meet the threshold criteria are de-flagged (i.e. de-selected).

The system and method of the present invention can also include provisions for identifying a group of flagged matrix elements having any intensity representing pixel values associated with the $M_x$ by $M_y$ pixel block corresponding to the flagged matrix element which are shared with another $M_x$ by $M_y$ pixel block corresponding to a different flagged matrix element. It is then determined which of these flagged matrix elements are greater than the others, or are positioned in the center of a group of elements each having identical values. Any of the flagged matrix elements which were not determined to be greater, or in the center position, are de-flagged.

Further, the system and method can include a provision for determining if a $M_x$ by $M_y$ pixel block corresponding to a flagged matrix element is within prescribed horizontal and vertical distance ranges from a $M_x$ by $M_y$ pixel block corresponding to another flagged matrix element. The prescribed horizontal distance range has an upper limit corresponding to the maximum expected horizontal eye separation of a subject and a lower limit corresponding to the minimum expected horizontal eye separation of a subject. Similarly, the prescribed vertical distance range has an upper limit corresponding to the maximum expected vertical eye separation of a subject and a lower limit corresponding to the minimum expected vertical eye separation of a subject.

Once the flagged matrix elements have been determined by the above-described processes, any $M_x$ by $M_y$ pixel block corresponding to a flagged matrix element can be designated as an actual subject eye location. However, it is preferred that further steps be taken to confirm the actual eye location, as well as to track the changing position of the subject's eye. Accordingly, it is preferred the system and method of the present invention include a provision for tracking the location of a center of each $M_x$ by $M_y$ pixel block potentially representing the image of the subject's pupil and at least the portion of the subject's iris in each subsequent image frame produced from the imaging apparatus. Further, a provision is preferably included to detect a blink at the location. Such a blink confirms the potential eye location is an actual eye location.

Generally, the aforementioned preferred provision for tracking and detecting a blink involves extracting a rectangular block of pixels centered at a current potential eye location. The current rectangular block is correlated with a block extracted during the aforementioned eye finding process. If the computed correlation coefficient does not exceed a threshold, then a blink has been detected. The center of the $M_x$ by $M_y$ pixel block corresponding to this location where a blink has been detected is then confirmed as an actual eye location.

More specifically, this preferred tracking and blink detecting provision involves first determining the center of the $M_x$ by $M_y$ pixel block associated with the previously-identified potential eye locations. Next, cut-out pixel blocks are selected in a next consecutive image frame produced by the imaging apparatus. Each of these cut-out pixel blocks respectively corresponds to the location of the $M_x$ by $M_y$ pixel block in the immediately preceding image frame which was identified as a potential eye location (i.e. the pixel block potentially representing the image of the subject's pupil and at least the portion of the subject's iris) and includes a number of pixels which surround the identified pixel block. Preferably, the number of pixels equates to the pixels contained in all surrounding $M_x$ by $M_y$ pixel blocks which are adjacent to the identified pixel block. Next, respective matrices of intensity representing pixel values are formed from an area surrounding the center of each $M_x$ by $M_y$ pixel block identified as a potential eye location in the last preceding image frame in which such a center was determined. Preferably, this area encompasses the identified pixel block and all surrounding adjacent pixel block of the same size. The appropriate one of these matrices is then correlated with each element of the associated cutout block. This correlation is performed by sequentially overlaying the center element of the appropriate one of the matrices onto each pixel value of the associated cut-out block starting with the upper left-hand corner, and performing a correlation between the overlaid matrix and the cut-out block for each overlaid cut-out block pixel location. The result of this correlation is to create a matrix of correlation coefficients associated with each cut-out block. These correlation coefficient matrices are compared to a correlation threshold value, and any correlation coefficient matrix element which exceeds the correlation threshold value in each of the correlation coefficient matrices is flagged. The correlation coefficient threshold value is chosen so as to ensure a substantial degree of correlation between an overlaid matrix and an associated cut-out block. If more than one element of a correlation coefficient matrix is flagged then it is determined which of the flagged correlation coefficient elements has the greatest value. This element having the greatest value in the matrix corresponds to the center pixel value of the $M_x$ by $M_y$ pixel block of the potential eye location in the image frame currently being processed. However, if no elements of a correlation coefficient matrix are flagged, then the lack of flagged elements condition in the matrix is noted and the number of consecutive times this condition has occurred is calculated. The aforementioned process is repeated for each consecutive image frame produced by the imaging apparatus to continuously track any movement of the potential eye locations.

The preferred provision for detecting that a blink has occurred in a location identified as potential eye is accomplished by monitoring the number of consecutive image frames which exhibit the aforementioned lack of flagged elements condition for a particular location. If this number does not exceed a prescribed threshold typical of a blink duration, for example approximately seven times in the tested embodiment, before elements of the correlation coefficient matrix corresponding to the location are once again flagged, then a blink has been detected. The center of the $M_x$ by $M_y$ pixel block corresponding the this location where a blink has been detected is then confirmed as an actual subject eye location.

The system and method may also have a provision for assigning a low confidence status to a location identified as a potential eye location whenever the number of consecutive times the aforementioned lack of flagged elements condition is detected for a correlation coefficient matrix associated with the location exceeds a prescribed threshold value, for example 150 times in the tested embodiment. This low confidence status indicates the location is not likely to be an actual subject's eye. Further, a low confidence status is assigned to a potential eye location whenever a blink is not detected at the location for a prescribed number of consecutive image frames (e.g. 150 frames in the tested embodiment). Finally, a low confidence status is also assigned to a location previously identified as an actual eye location whenever the number of consecutive times the lack of flagged elements condition associated with this location exceeds a prescribed threshold (for example 150 times in the tested embodiment) and there is no other location identified as an actual eye location within the previously-described horizontal and vertical distance ranges from the actual eye location. The system is reinitialized whenever all the locations identified as potential or actual eye locations are assigned a low confidence status.

In addition to the just described benefits, other objectives and advantages of the present invention will become apparent from the detailed description which follows hereinafter when taken in conjunction with the drawing figures which accompany it.

DESCRIPTION OF THE DRAWINGS

The specific features, aspects, and advantages of the present invention will become better understood with regard to the following description, appended claims, and accompanying drawings where:

DETAILED DESCRIPTION OF THE PREFERRED EMBODIMENTS

In the following description of the preferred embodiments of the present invention, reference is made to the accompanying drawings which form a part hereof, and in which is shown by way of illustration specific embodiments in which the invention may be practiced. It is understood that other embodiments may be utilized and structural changes may be made without departing from the scope of the present invention.

Figure 1:
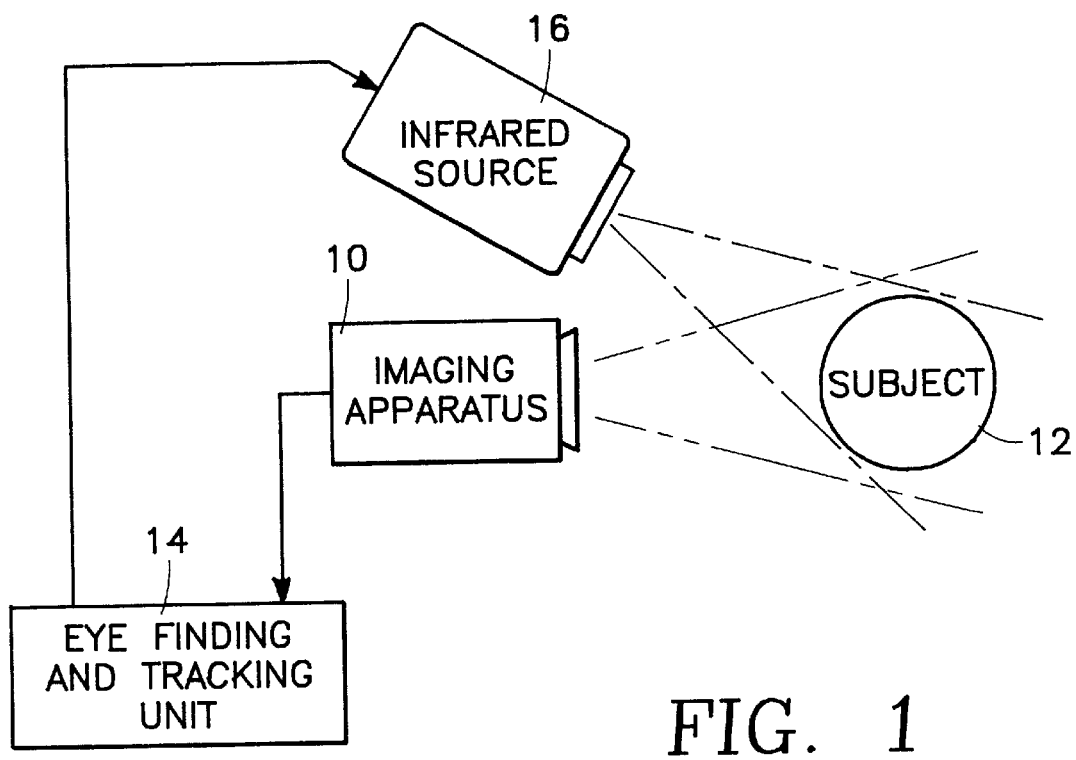
FIG. 1 is a schematic diagram showing one embodiment of an eye finding and tracking system in accordance with the present invention.

FIG. 1 depicts an eye finding system embodying the present invention. The system includes an imaging apparatus 10 which may be a digital camera, or a television camera connected to a frame grabber device as is known in the art. The imaging apparatus 10 is located in front of a subject 12, so as to image his or her face. Thus, the output of the imaging apparatus 10 is a signal representing digitized images of a subject's face. Preferably, the digitized images are provided at a rate of about 30 frames per second. Each frame preferably consists of an 640 by 480 array of pixels each having one of 256 (i.e. 0 to 255) gray tones representative of the intensity of reflected light from a portion of the subject's face. The output signal from the imaging apparatus is fed into an eye finding and tracking unit 14. The unit 14 processes each image frame produced by the imaging apparatus 10 to detect the position of the subject's eye and to track these eye positions over time. The eye finding and tracking unit 14 can employ a digital computer to accomplish the image processing task, or alternately, the processing could be performed by logic circuitry specifically designed for the task. Optionally, there can also be an infrared light source 16 positioned so as to illuminate the subject's face. The eye finding and tracking unit 14 would be used to control this light source 16. The infrared light source 16 is activated by the unit 14 whenever it is needed to effectively image the subject's face. Specifically, the light source would be activated to illuminate the subject's face at night or when the ambient lighting conditions are too low to obtain an image. The unit 14 includes a sensor capable of determining when the ambient lighting conditions are inadequate. In addition, the light source would be employed when the subject 12 is wearing non-reflective sunglasses, as these types of sunglasses are transparent to infrared light. The subject could indicate that sunglasses are being worn, such as by depressing a control switch on the eye finding and tracking unit 14, thereby causing the infrared light source 16 to be activated. Alternately, the infrared light source 16 could be activated automatically by the unit 14, for example, when the subject's eyes cannot be found otherwise. Of course, if an infrared light source 16 is employed, the imaging apparatus 10 would be of the type capable of sensing infrared light.

Figure 2:
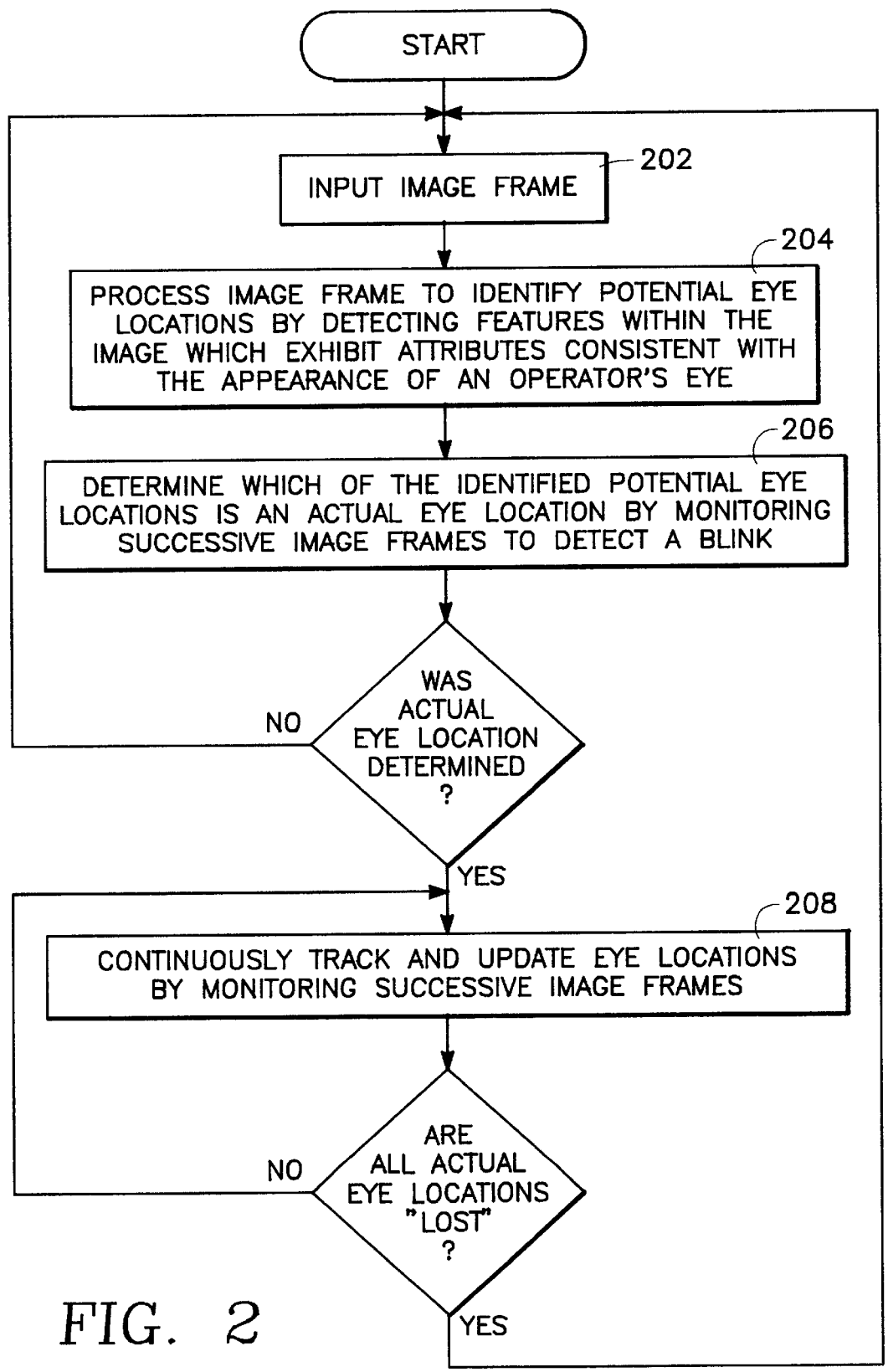
FIG. 2 is a preferred overall flow diagram of the process used in the eye finding and tracking unit of FIG. 1.

FIG. 2 is an overall flow diagram of the preferred process used to find and track the location of a subject's eyes. At step 202, a first image frame of the subject's face is inputted from the imaging apparatus to the eye finding and tracking unit. At step 204, the inputted image frame is processed to identify potential eye locations. This is accomplished, as will be explained in detail later, by identifying features within the image frame which exhibit attributes consistent with those associated with the appearance of a subject's eye. Next, in step 206, a determination is made as to which of the potential eye locations is an actual eye of the subject. This is generally accomplished by monitoring successive image frames to detect a blink. If a blink is detected at a potential eye location, it is deemed an actual eye location. This monitoring and blink detection process will also be described in detail later. At step 208, the now determined actual eye locations are continuously tracked and updated using successive image frames. In addition, if the location of the actual eye locations are not found or are lost, the process is reinitialized by returning to step 202 and repeating the eye finding procedure.

Figure 3A:
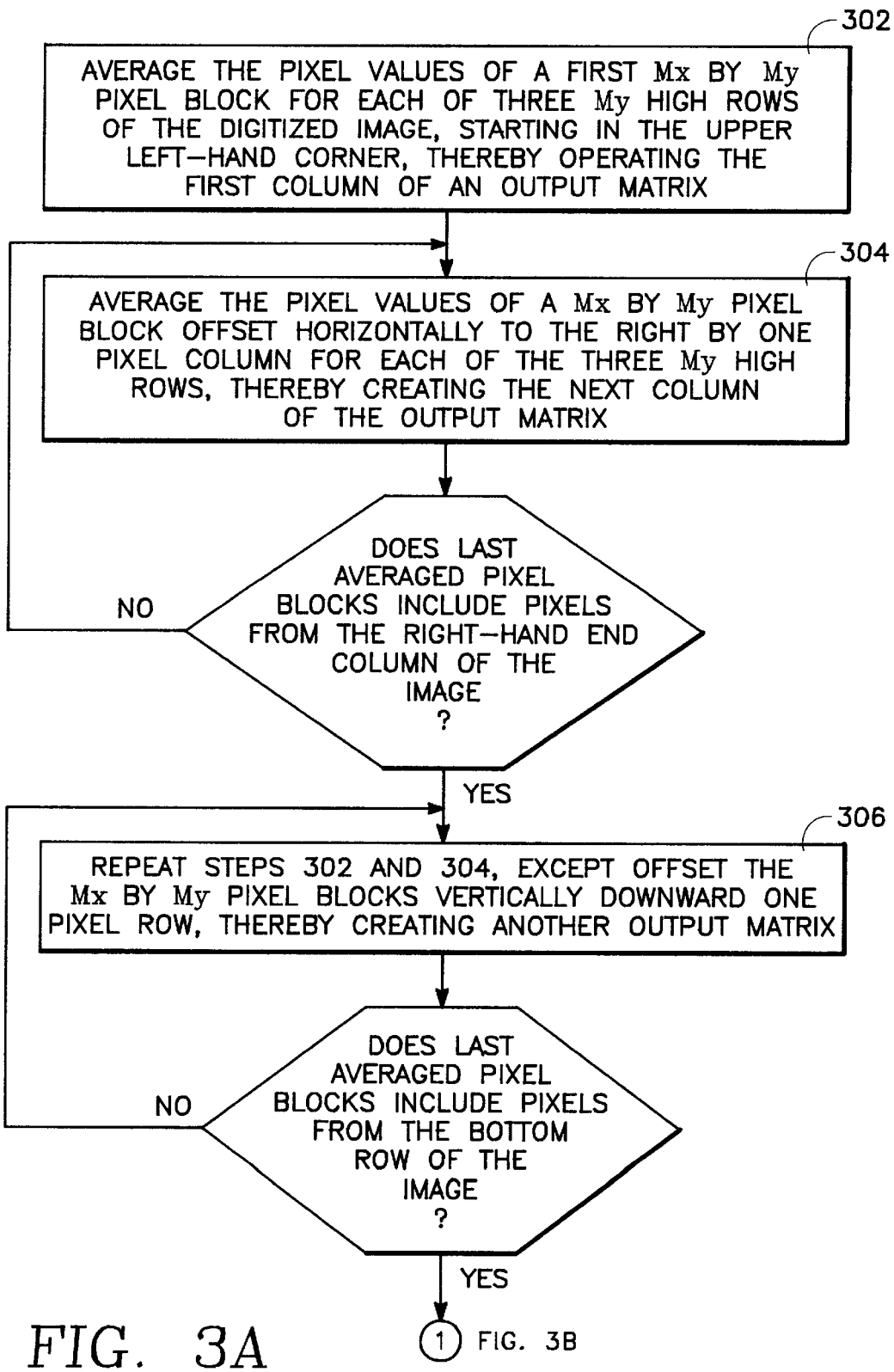
FIG. 3 is a flow diagram of a process for identifying potential eye locations (and optionally actual eye locations) within an image frame produced by the imaging apparatus of FIG. 1.
Figure 3B:
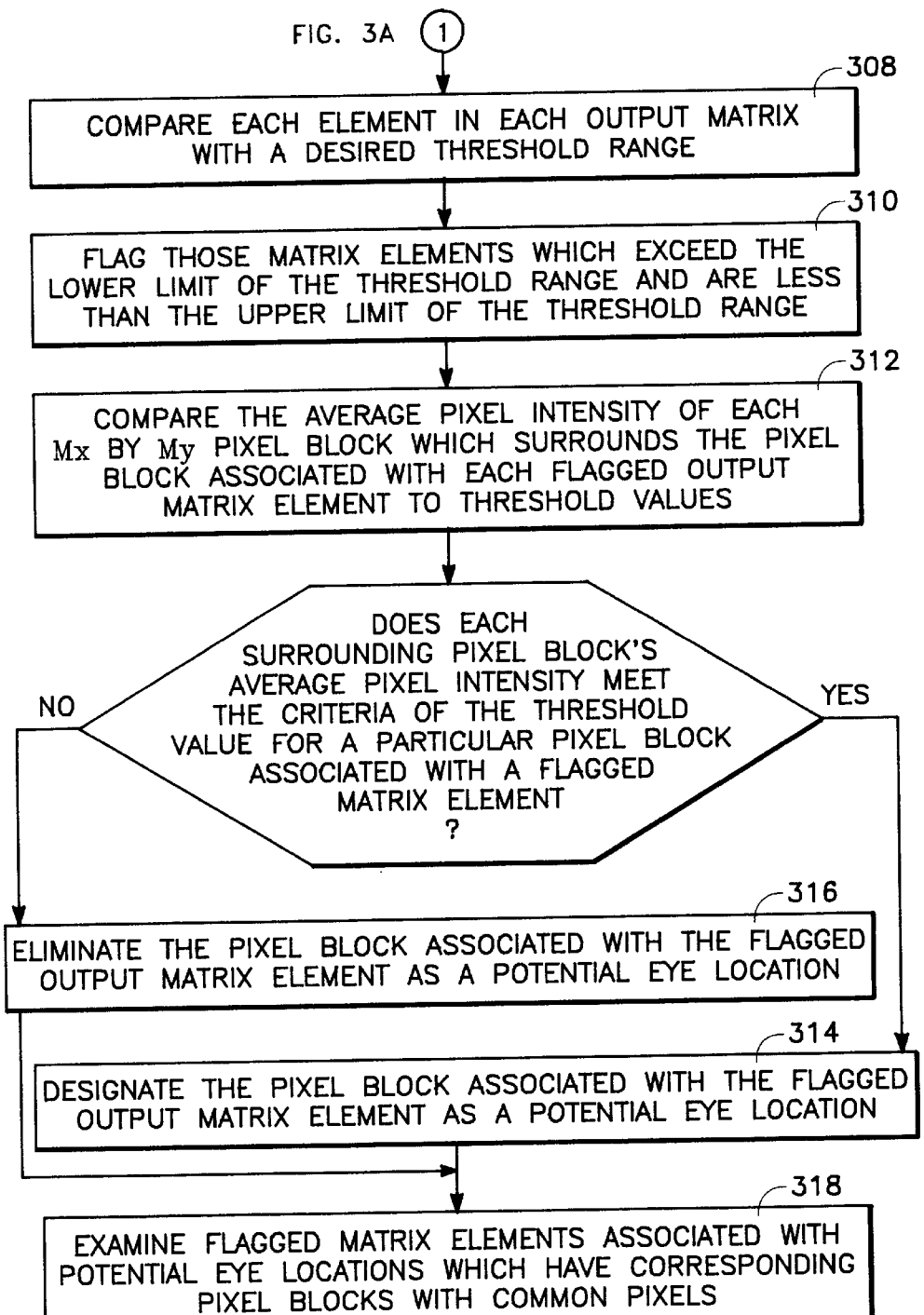
Figure 3C:
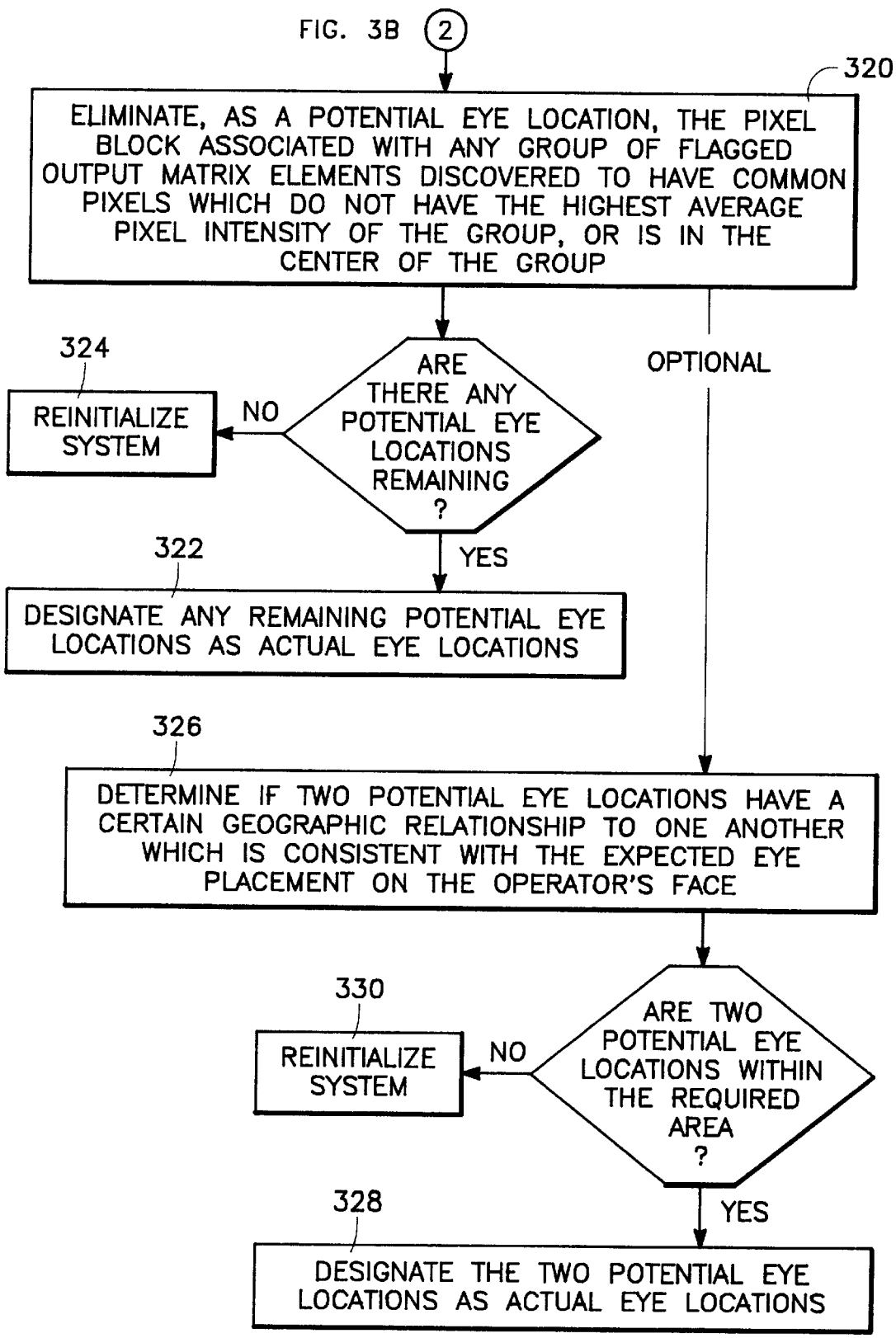
Figure 4:
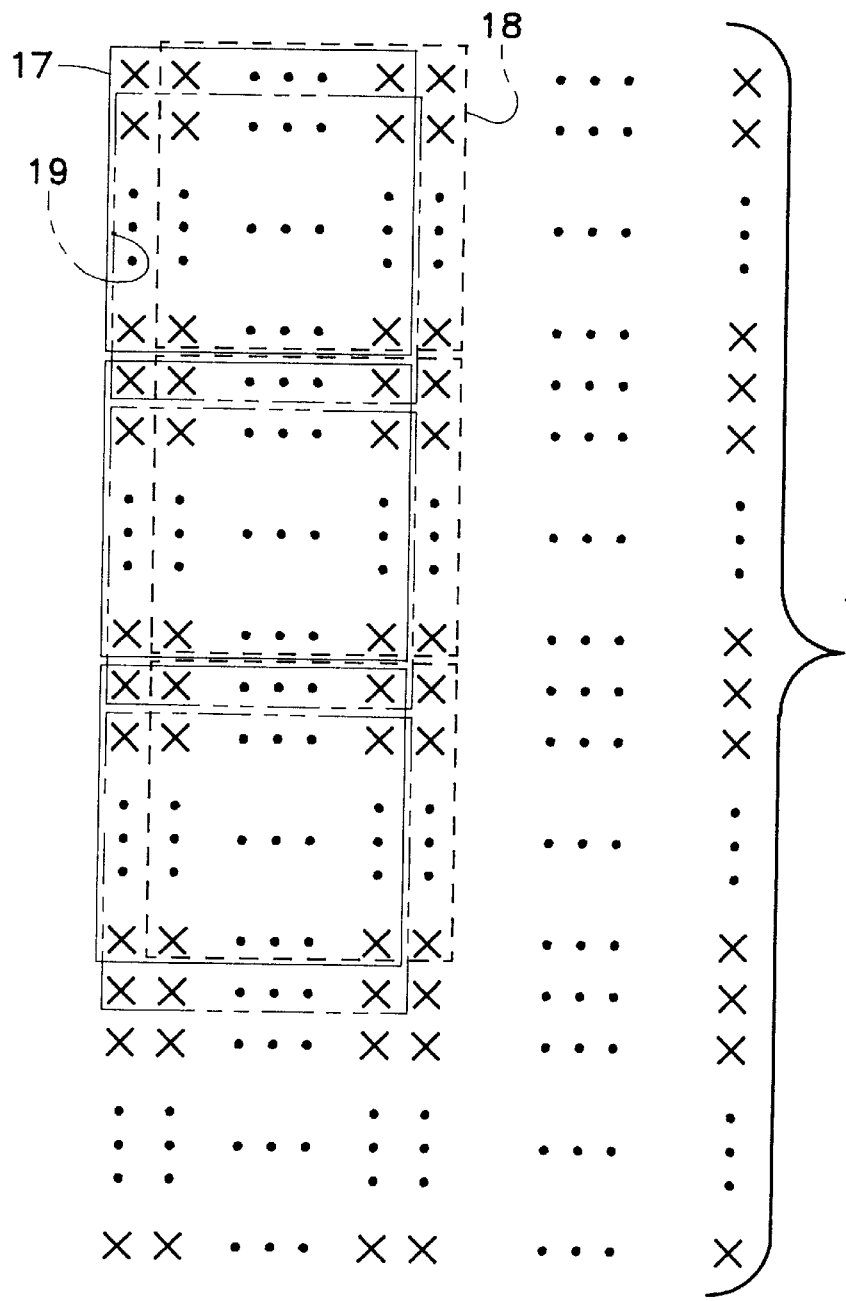
FIG. 4 is an idealized diagram of the pixels in an image frame including various exemplary pixel block designations applicable to the process of FIG. 3.

FIG. 3 is a flow diagram of the process used to identify potential eye locations in the initial image frame. The first step 302 involves averaging the digitized image values which are representative of the pixel intensities of a first $M_x$ by $M_y$ block of pixels for each of three $M_y$ high rows of the digitized image, starting in the upper left-hand corner of the image frame, as depicted by the solid line boxes 17 in FIG. 4. The three averages obtained in step 302 are used to form the first column of an output matrix. The $M_x$ variable represents a number of pixels in the horizontal direction of the image frame, and the $M_y$ variable represents a number of pixels in the vertical direction of the image frame. These variables are preferably chosen so that the resulting $M_x$ by $M_y$ pixel block has a size which just encompasses the minimum expected size of the iris and pupil portions of a subject's eye. In this way, the pixel block would contain an image of the pupil and at least a part of the iris of any subject's eye.

Once the first column of the output matrix has been created by averaging the first three $M_x$ by $M_y$ pixel blocks in the upper right-hand portion of the image frame, the next step 304 is to create the next column of the output matrix. This is accomplished by averaging the intensity representing values of a $M_x$ by $M_y$ pixel block which is offset horizontally to the right by one pixel column from the first pixel block for each of the three aforementioned $M_y$ high rows, as shown by the broken line boxes 18 in FIG. 4. This process is repeated, moving one pixel column to the right during each iteration, until the ends of the three $M_y$ high rows in the upper portion of the image frame are reached. The result is one completed output matrix. The next step 306 in the process is to repeat steps 302 and 304, except that the $M_x$ by $M_y$ pixel blocks being averaged are offset vertically downward from the previous pixel blocks by one pixel row, as depicted by the dashed and dotted line boxes 19 in FIG. 4. This produces a second complete output matrix. This process of offsetting the blocks vertically downward by one pixel row is then continued until the bottom of the image frame is reached, thereby forming a group of output matrices. The purpose of averaging three $M_y$ high blocks at once is to compensate for any geometrical distortion caused by, for example, head movements due to vibration of the vehicle.

In step 308, each element of each output matrix in the group of generated output matrices is compared with a threshold range. Those matrix elements which exceed the lower limit of the threshold range and are less than the upper limit of this range, are flagged (step 310). The upper limit of the threshold range corresponds to a value which represents the maximum expected average intensity of a $M_x$ by $M_y$ pixel block containing an image of the iris and pupil of a subject's eye for the illumination conditions that are present at the time the image was captured. The maximum average intensity of block containing the image of the subject's pupil and at least a portion of the iris will be lower than the same size portion of most other areas of the subject's face because the pupil absorbs a substantial portion of the light impinging thereon. Thus, the upper threshold limit is a good way of eliminating portions of the image frame which cannot be the subject's eye. However, it must be noted that there are some things that could be in the image of the subject's face which do absorb more light than the pupil. For example, black hair can under some circumstances absorb more light. In addition, if the image is taken at night, the background surrounding the subject's face could be almost totally black. The lower threshold limit is employed to eliminate these portions of the image frame which cannot be the subject's eye. The lower limit corresponds to a value which represents the minimum expected average intensity of a $M_x$ by $M_y$ pixel block containing an image of the pupil and at least a portion of the subject's iris. Here again, this minimum is based on the illumination conditions that are present at the time the image is captured.

Next, in step 312, the average intensity value of each $M_x$ by $M_y$ pixel block which surrounds the $M_x$ by $M_y$ pixel block associated with each of the flagged output matrix elements is compared to an output matrix threshold value. In one embodiment of the present invention, this threshold value represents the lowest expected average intensity possible for the pixel block sized areas immediately adjacent the portion of an image frame containing the subject's pupil and iris. Thus, if the average intensity of the surrounding pixel blocks exceeds the threshold value, then a reasonably high probability exists that the flagged block is associated with the location of the subject's eye. Thus, the pixel block associated with the flagged element is designated a potential eye location (step 314). However, if one or more of the average intensity values for the blocks surrounding the flagged block falls below the threshold, then the flagged block is eliminated as a potential eye location (step 316). This comparison concept is taken further in a preferred embodiment of the present invention where a separate threshold value is applied to each of the surrounding pixel block averages. This has particular utility because some of the areas immediately surrounding the iris and pupil exhibit unique average intensity values which can be used to increase the confidence that the flagged pixel block is good prospect for a potential eye location. For example, the areas immediately to the left and right of the iris and pupil include the white parts of the eye. Thus, these areas tend to exhibit a greater average intensity than most other areas of the face. Further, it has been found that the areas directly above and below the iris and pupil are often in shadow. Thus, the average intensity of these areas is expected to be less than many other areas of the face, although greater than the average intensity of the portion of the image containing the iris and pupil. Given the aforementioned unique average intensity profile of the areas surrounding the iris and pupil, it is possible to chose threshold values to reflect these traits. For example, the threshold value applied to the average intensity value of the pixel blocks directly to the left and right of the flagged block would be just below the minimum expected average intensity for these relatively light areas of the face, and the threshold value applied to the average intensity values associated with the pixel block directly above and below the flagged block would be just above the maximum expected average intensity for these relative dark regions of the face. Similarly, the pixel blocks diagonal to the flagged block would be assigned threshold values which are just below the minimum expected average intensity for the block whenever the average intensity for the block is generally lighter than the rest of the face, and just above the maximum expected average intensity for a particular block if the average intensity of the block is generally darker than the rest of the face. If the average intensity of the "lighter" blocks exceeds the respectively assigned threshold value, or the "darker" blocks are less than the respectively assigned threshold value, then the flagged pixel block is deemed a potential eye location. If any of the surrounding pixel blocks do not meet this thresholding criteria, then the flagged pixel block is eliminated as a potential eye location.

Of course, because the output matrices were generated using the previously-described "one pixel column and one pixel row offset" approach, some of the matrices will contain rows having identical elements as others because they characterize the same pixels of the image frame. This does not present a problem in identifying the pixel block locations associated with potential eye locations as the elements flagged by the above-described thresholding process in multiple matrices which correspond to the same pixels of the image frame will be identified as a single location. If fact, this multiplicity serves to add redundancy to the identification process. However, it is preferred that the pixel block associated with a flagged matrix element correspond to the portion of the image centered on the subject's pupil. The aforementioned "offset" approach will result in some of the matrices containing elements which represent pixel blocks that are one pixel column or one pixel row removed from the block containing the centered pupil. Thus, the average intensity value of these blocks can be quite close, or even identical, to that of the block representing the centered pupil. Thus, the matrix elements representing these blocks may also be identified as potential eye locations via the above-described thresholding process. To compensate, the next step 318 in the process of identifying potential eye locations is to examine flagged matrix elements associated with the previously-designated potential eye locations which correspond to blocks having pixels in common with pixel blocks associated with other flagged elements. Only the matrix element representing the block having the minimum average intensity among the examined group of elements, or which is centered within the group, remain flagged. The others are de-selected and no longer considered potential eye locations (step 320).

Any remaining potential eye locations identified in the above process could be considered the actual eye locations with a reasonable amount of confidence, especially, if the more sophisticated and preferred thresholding processes are employed (step 322). If, however, no remaining potential eye locations exist, then the system is reinitialized in step 324 by inputting a next image frame and starting over at step 302.

The confidence level could optionally be further increased by determining if two of the remaining potential eye locations have a certain geographic relationship to each other (step 326). If so, these two potential eye locations are designated as actual eye locations (step 328). An example of a process for determining if two potential eye locations have the desired geographic relationship involves determining if the locations are within a prescribed horizontal and vertical (i.e. to allow for the head being cocked) distance range from one another. These distance ranges represent the difference between the minimum and maximum expected horizontal and vertical eye separation typical of the subject being monitored (e.g. an adult vehicle operator). If the potential eyes are within these distance ranges, then the chances that these locations are actual eyes is increased. Performing the required distance measurements from a digitized image can be accomplished using any appropriate conventional imaging technique. In the case where none of the remaining potential eye locations are within the aforementioned geographic relationship to one another, then the system is reinitialized in step 330 by inputting a next image frame and starting over at step 302.

However, in a more preferred embodiment of the present invention, it is desired that the confidence level be increase even further by observing subsequent image frames in order to detect a blink, i.e. a good indication a potential eye location is an actual eye location. A preliminary determination in this blink detecting process (and as will be seen the eye tracking process) is to identify the image pixel in the original image frame which constitutes the center of the pupil of each identified potential eye location. As the pixel block associated with the identified potential eye location should be centered on the pupil, finding the center of the pupil can be approximated by simply selecting the pixel representing the center of the pixel block. Alternately, a more intensive process can be employed to ensure a the accuracy of the identified pupil center location. This is accomplished by first, comparing each of the pixels in an identified block to a threshold value, and flagging those pixels which fall below this threshold value. The purpose of applying the threshold value is to identify those pixel of the image which correspond to the pupil of the eye. As the pixels associated with the pupil image will have a lower intensity than the surrounding iris, the threshold value is chosen to approximate the highest intensity expected from the pupil image for the illumination conditions present at the time the image was captured. This ensures that only the darker pupil pixels are selected and not the pixels imaging the relatively lighter surrounding iris structures. Once the pixels associated with the pupil are flagged, the next step is to determine the geographic center of the selected pixels. This geographic center will be the pixel of the image which represents the center of the pupil, as the pupil is circular in shape. The geographic center of the selected pixels can be accomplished in a variety of ways. For example, the pixel block associated with the potential eye location can be scanned horizontally, column by column, until one of the selected pixels is detected within a column. This column location is noted and the horizontal scan is continued until a column containing no selected pixels is found. This second column location is also noted. A similar scanning process is then conducted vertically, so as to identify the first row in the block containing a selected pixel and the next subsequent row containing no selected pixels. The center of the pupil is chosen as the pixel having a column location in-between the noted columns and a row location in-between the noted rows. Any noise in the image or spots in the iris, which are dark enough to be selected in the aforementioned thresholding step, can skew the results of the just-described process. However, this possibility can be eliminated in a number of way, for example by requiring there be a prescribed number of pixel columns or rows following the first detection before that column or row is noted as the outside edge of the pupil.

A blink at a potential eye location represents itself as a brief period where the eyelid is closed, e.g. about 2–3 image frames in length based on an imaging system producing about 30 frames per second. This would appear as a "disappearance" of a potential eye at an identified location for a few successive frames, followed by its "reappearance" in the next frame. The eye "disappears" from an image frame during the blink because the eyelid which covers the iris and pupil will exhibit a much greater average pixel intensity. Thus, the closed eye will not be detected by the previously-described thresholding process. Further, it is noted that when the eye opens again after the completion of the blink, it will be in approximately the same location as identified prior to the blink if a reasonable frame speed is employed by the imaging system. For example, a 30 frames per second rate is adequate to ensure the eye has not moved significantly in the 2–3 frames it takes to blink, Any slight movement of the eye is detected and compensated for by a correlation procedure to be described shortly.

Figure 5A:
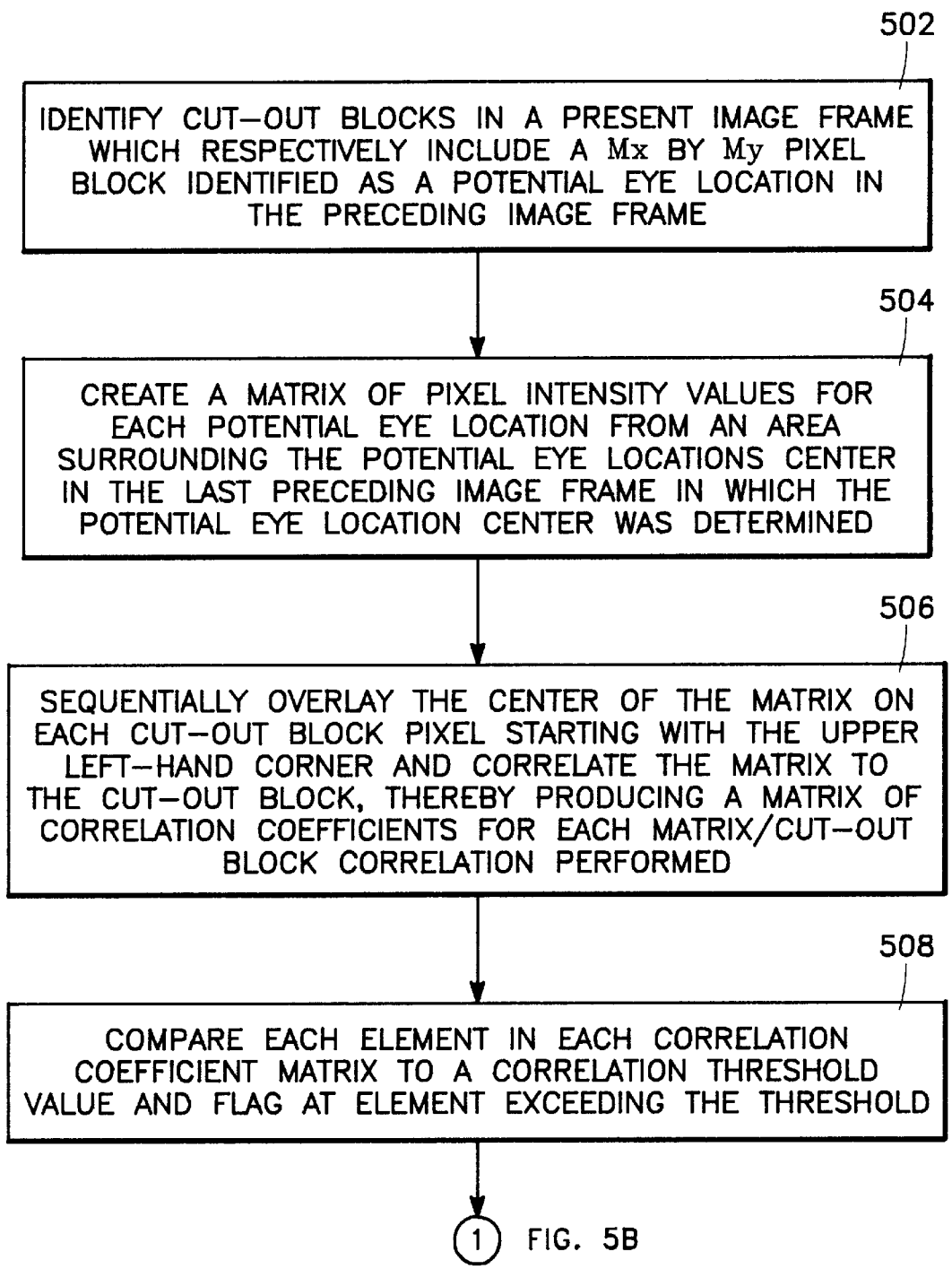
FIG. 5 is a flow diagram of a process for tracking eye locations in successive image frames produced by the imaging apparatus of FIG. 1, as well as a process of detecting a blink at a potential eye location to identify it as an actual eye location.
Figure 5B:
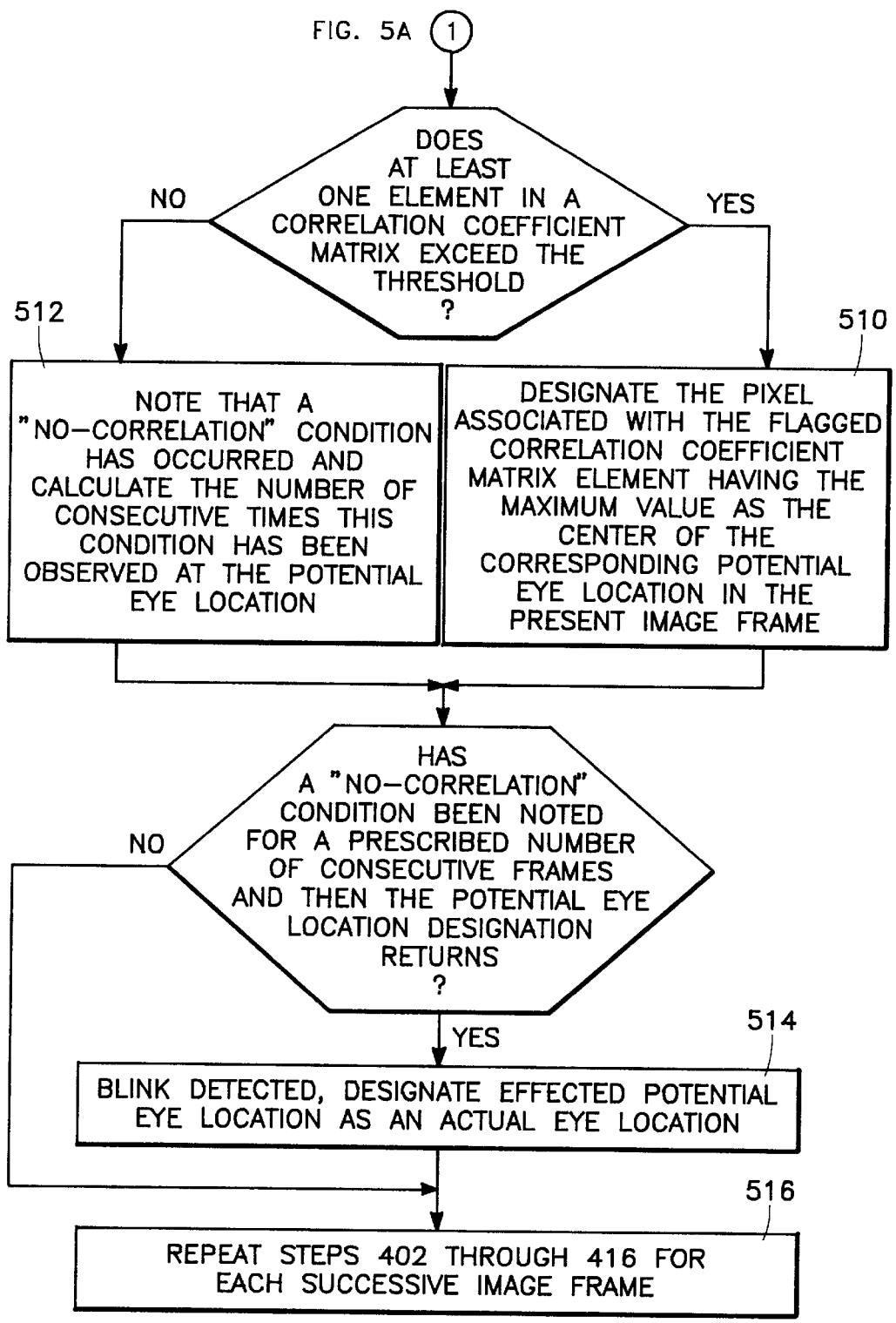
Figure 6:
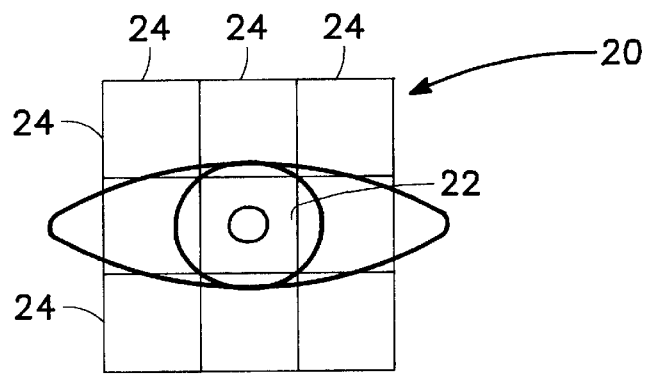
FIG. 6 is a diagram showing a cut-out block of an image frame applicable to the process of FIG. 5.

The subsequent image frames could be processed as described above to re-identify potential eye locations which would then be correlated to the locations identified in previous frames in order to track the potential eyes in anticipation of detecting a blink. However, processing the entire image in subsequent frames requires considerable processing power and may not provide as accurate location data as the preferred method of the present invention. FIG. 5 is a flow diagram of the preferred eye location tracking and blink detection process used primarily to identify and track actual eye locations among the potential eye locations identified previously (i.e. steps 302 through 320 of FIG. 3). This preferred process uses cut-out blocks in the subsequent frames which are correlated to the potential eye locations in the previous frame to determine a new eye location. Processing just the cutout blocks rather than the entire image saves considerable processing resources. The first step 502 in the process involves identifying the aforementioned cut-out blocks within the second image frame produced by the imaging system. This is preferably accomplished by identifying cut-out pixel blocks 20 in the second frame, each of which includes the pixel block 22 corresponding to the location of the block identified as a potential eye location in the previous image frame, and all adjacent $M_x$ by $M_y$ pixel blocks 24, as shown in FIG. 6. Next, in step 504, a matrix is created from the first image for each potential eye location. This matrix includes all the represented pixel intensities in an area surrounding the determined center of a potential eye location. Preferably, this area is bigger than the cut-out block employed in the second image. For example, an area having a size of 100 by 50 could be employed. The center element of each matrix (which corresponds to the determined center of the pupil of the potential eye) is then "overlaid" in step 506 on each pixel in the associated cut-out block in the second image frame, starting with the pixel in the upper left-hand corner. A correlation procedure is then performed between each matrix and the overlaid pixels of its associated cutout block. This correlation is accomplished using any appropriate conventional matrix correlation process. As these correlation processes are known in the art, no further detail will be provided herein. The result of the correlation is a correlation coefficient representing the degree to which the pixel matrix from the first image frame corresponded to the overlaid position in the associated cutout block. This process is repeated for all the pixel locations in each cut-out block to produce a correlation coefficient matrix for each potential eye location. In step 508, a threshold value is compared to each element in the correlation coefficient matrices, and those which exceed the threshold are flagged. The flagged element in each of these correlation coefficient matrices which is larger than the rest of the elements corresponds to the pixel location in the second image which most closely matches the intensity profile of the associated potential eye location identified in the first image, and represents the center of the updated potential eye location in the second image frame. If such a maximum value is found, the corresponding pixel location in the second image is designated as the new center of the potential eye location (step 510). The threshold value was applied to ensure the pixel intensity values in the second frame were at least "in line" with those in the corresponding potential eye locations in the first image. Thus, the threshold is chosen so as to ensure a relatively high degree of correlation is observed. For example, a threshold value of at least 0.5 could be employed.

If none of the correlation coefficients exceeded the correlation threshold in a given iteration of the tracking procedure, then this is an indication the eye has been "lost", or perhaps a blink is occurring. This "no-correlation" condition is noted. Subsequent frames are then monitored and the number of consecutive times the "no-correlation" condition occurs is calculated in step 512. Whenever, a no-correlation condition exists from a period of 2–3 frames, and then the potential eye is detected once again, this is indicative of a blink. If a blink is so detected, the status of the potential eye location is upgraded to a high confidence actual eye location (step 514). This is possible because an eye will always exhibit this blink response, and so the location can be deemed that of an actual eye with a high degree of confidence. The eye tracking and blink detection process (of FIG. 5) is repeated for each successive frame generated by the imaging apparatus with the addition that actual eye locations are tracked as well as the remaining potential eye locations (step 516). This allows the position of the actual and potential eye locations to be continuously updated. It is noted that the pixel matrix from the immediately preceding frame is used for the aforementioned correlation procedure whenever possible. However, where a no-correlation condition exists in any iteration of the tracking process, the present image is correlated using the pixel matrix from the last image frame where the affected eye location was updated.

Figure 7B:
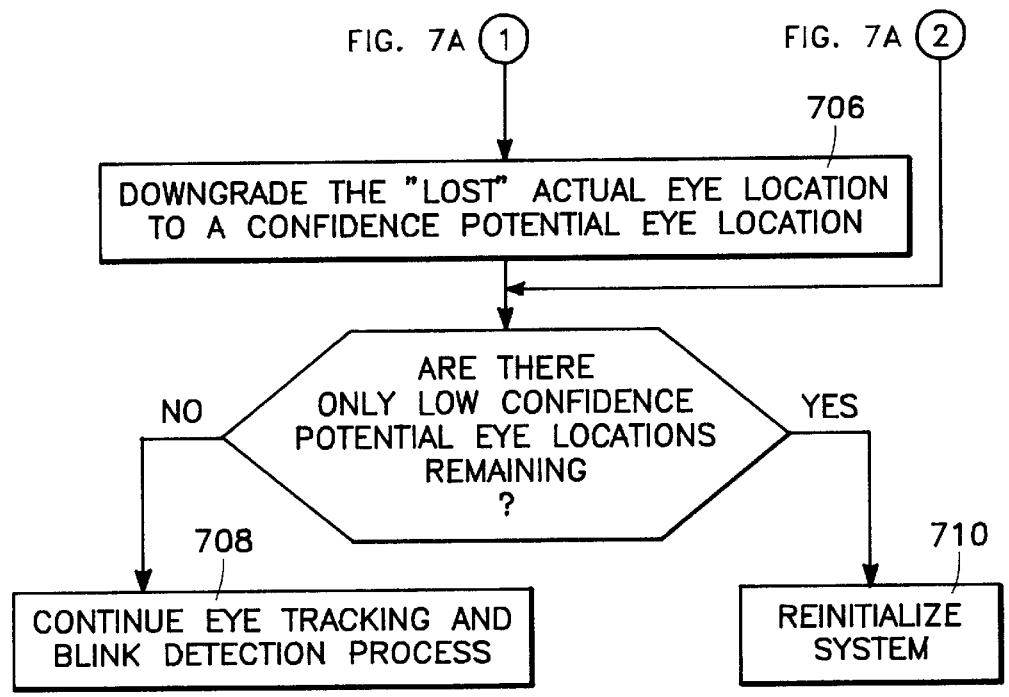
FIG. 7 is a flow diagram of a process for monitoring potential and actual eye locations and to reinitialize the eye finding and tracking system if all monitored eye locations are deemed low confidence locations.
Figure 7A:
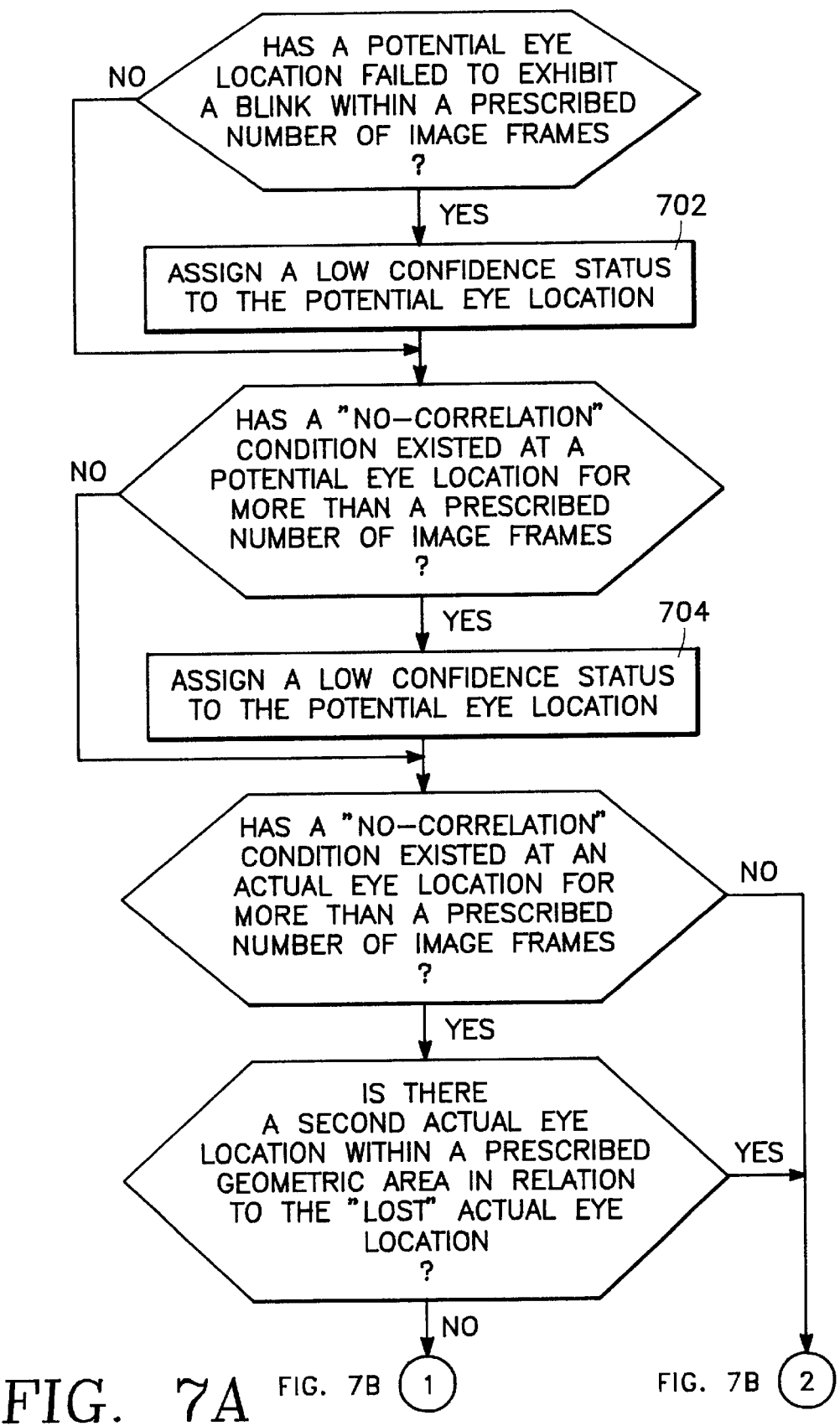

Referring now to FIG. 7, if a potential eye location does not exhibit a blink response within 150 image frames, it is still tracked but assigned a low confidence status (i.e. a low probability it is an actual eye location) at step 702. Similarly, if a potential eye location becomes "lost" in that there is a no-correlation condition for more than 150 frames, this location is assigned a low confidence status (step 704). Further, if a blink has been detected at a potential eye location and its status upgraded to an actual eye location, but then this location is "lost", its status will depend on a secondary factor. This secondary factor is the presence of a second actual eye location having a geometric relationship to the first, as was described previously. If such a second eye location exists, the high confidence status of the "lost" actual eye does not change. If, however, there is no second eye location, then the "lost" actual eye is downgraded to a low confidence potential eye location (step 706). The determination of high and low confidence is important because, the tracking process continues for all potential or actual eye locations only for as long as there is at least one remaining high confidence actual eye location or an un-designated potential eye location (i.e. a potential eye location which has not been assigned a low confidence status) being monitored (step 708). However, if only low confidence locations exist, the system is re-initialized and the entire eye finding and tracking process starts over (step 710).

While the invention has been described in detail by reference to the preferred embodiment described above, it is understood that variations and modifications thereof may be made without departing from the true spirit and scope of the invention.

Wherefore, what is claimed is:

1. A method of finding and tracking the location of a subject's eyes, comprising the steps of:

employing an imaging apparatus which produces digital image frames including the face and eyes of a subject, each digital image frame comprising an array of pixel values representing the intensity of light reflected from the face of the subject, wherein each intensity representing pixel value is located at a position in the array specified by x and y coordinates;

averaging the intensity representing pixel values within respective $M_x$ by $M_y$ pixel blocks of a digitized image frame to create elements of output matrices; and comparing elements of the output matrices to threshold values, said threshold values being chosen so as to identify which matrix elements correspond to a $M_x$ by $M_y$ pixel block which includes pixel values potentially representing an image of the subject's pupil and at least the portion of the subject's iris.

2. The method of claim 1, wherein said averaging step comprises the steps of:

(a) respectively averaging the intensity representing pixel values within three vertically arranged $M_x$ by $M_y$ pixel blocks in the upper left-hand corner of said digitized image frame to create a first three-element column of an output matrix;

(b) respectively averaging the intensity representing pixel values within three vertically arranged $M_x$ by $M_y$ pixel blocks each of which is offset to the right by one column of the array in relation to a last averaged pixel block to create a new column of the output matrix; and (c) repeating step (b) until three vertically arranged $M_x$ by $M_y$ pixel blocks which include pixel values from the last column of the array have been averaged to create a last column of the output matrix.

3. The method of claim 2, wherein said averaging step further comprises the steps of:

(d) respectively averaging the intensity representing pixel values within three vertically arranged $M_x$ by $M_y$ pixel blocks starting at a position on the left-hand side of the array which is offset downward by one row in relation to a previously averaged pixel block to create a first three-element column of a new output matrix;

(e) respectively averaging the intensity representing pixel values within three vertically arranged $M_x$ by $M_y$ pixel blocks each of which is offset to the right by one column of the array in relation to a last averaged pixel block to create a new column of the new output matrix;

(f) repeating step (e) until three vertically arranged $M_x$ by $M_y$ pixel blocks which include pixel values from the last column of the array have been averaged to create a last column of the new output matrix; and (g) repeating steps (d) through (f) until three vertically arranged $M_x$ by $M_y$ pixel blocks which include pixel values from the last column and row of the array have been averaged to create a last column of a last new output matrix.

4. The method of claim 3, wherein said comparing step comprises the steps of:

(h) comparing each element of each output matrix to a threshold range;

(i) flagging any output matrix element which both exceeds a lower limit of the threshold range and is less than an upper limit of the threshold range;

(j) comparing a threshold value to the average of the intensity representing pixel values within each $M_x$ by $M_y$ pixel block immediately surrounding any pixel block corresponding to an output matrix element flagged in step (i).

5. The method of claim 4, wherein said threshold range comprises:

a lower limit representing the lowest expected average of the intensity representing pixel values within a $M_x$ by $M_y$ pixel block corresponding to an image of the subject's pupil and at least a portion of the subject's iris for the particular illumination condition present at the time the image was produced; and an upper limit representing the highest expected average of the intensity representing pixel values within the $M_x$ by $M_y$ pixel block corresponding to the image of the subject's pupil and at least the portion of the subject's iris for the particular illumination condition present at the time the image was produced.

6. The method of claim 4, wherein the same threshold value is compared to the average of the intensity representing pixel values associated with each $M_x$ by $M_y$ pixel block immediately surrounding any pixel block corresponding to a flagged output matrix element, and wherein said threshold value comprises a lowest expected average of the intensity representing pixel values within any $M_x$ by $M_y$ pixel block immediately surrounding a $M_x$ by $M_y$ pixel block corresponding to an image of the subject's pupil and at least a portion of the subject's iris for the particular illumination condition present at the time the image was produced, and wherein the comparing step further comprises:

(k) de-flagging any previously flagged output matrix element which has any surrounding pixel block which fails to exceed the threshold value.

7. The method of claim 4, wherein a different threshold value is compared to the average of the intensity representing pixel values associated with each $M_x$ by $M_y$ pixel block immediately surrounding any pixel block corresponding to a flagged output matrix element, and wherein the respective threshold value comprises a lowest expected average of the intensity representing pixel values within the associated $M_x$ by $M_y$ pixel block immediately surrounding a central $M_x$ by $M_y$ pixel block corresponding to an image of the subject's pupil and at least a portion of the subject's iris for the particular illumination condition present at the time the image was produced in immediately surrounding pixel blocks which exhibit an average intensity exceeding that of an average intensity of said digitized image frame, and a highest expected average of the intensity representing pixel values within the associated $M_x$ by $M_y$ pixel block immediately surrounding the central $M_x$ by $M_y$ pixel block corresponding to the image of the subject's pupil and at least a portion of the subject's iris for the particular illumination condition present at the time the image was produced in immediately surrounding pixel blocks which exhibit an average intensity less than that of the average intensity of said digitized image frame, and wherein the comparing step further comprises:

(k) de-flagging any previously flagged output matrix element which has any surrounding pixel block which either (1) fails to exceed the threshold value in the immediately surrounding pixel blocks which exhibit an average intensity exceeding that of an average intensity of said digitized image frame, or (2) fails to be less than the threshold value produced in the immediately surrounding pixel blocks which exhibit an average intensity less than that of the average intensity of said digitized image frame.

8. The method of claim 4, further comprising the steps of:

(l) identifying groups of flagged matrix elements having any common intensity representing pixel values associated with the respective $M_x$ by $M_y$ pixel blocks corresponding to the flagged matrix elements;

(m) determining one of (1) which of the flagged matrix elements in each of said groups identified in step (l) are greater than the others, or (2) whenever no one element has the greatest value, which of the flagged matrix elements in each of said groups identified in step (l) is in the geometric center of the group; and (n) deflagging any of the flagged matrix elements identified in step (l) which were not determined to be greater or in the center in step (m).

9. The method of claim 8, further comprising the step of determining if a $M_x$ by $M_y$ pixel block corresponding to a flagged matrix element is within prescribed horizontal and vertical distance ranges from a $M_x$ by $M_y$ pixel block corresponding to another flagged matrix element, said prescribed horizontal distance range having an upper limit corresponding to the maximum expected horizontal eye separation of the subject and a lower limit corresponding to the minimum expected horizontal eye separation of the subject, and said prescribed vertical distance range having an upper limit corresponding to the maximum expected vertical eye separation of the subject and a lower limit corresponding to the minimum expected vertical eye separation of the subject.

10. The method of claim 9, further comprising the step of designating any $M_x$ by $M_y$ pixel block corresponding to a flagged matrix element as an actual eye location.

11. The method of claim 8, further comprising the step of designating any $M_x$ by $M_y$ pixel block corresponding to a flagged matrix element as an actual eye location.

12. A method of finding and tracking the location of a subject's eyes, comprising the steps of:

employing an imaging apparatus which produces digital image frames including the face and eyes of a subject, each digital image frame comprising an array of pixel values representing the intensity of light reflected from the face of the subject, wherein each intensity representing pixel value is located at a position in the array specified by x and y coordinates;

averaging the intensity representing pixel values within respective $M_x$ by $M_y$ pixel blocks of a first digitized image frame to create elements of output matrices;

comparing elements of the output matrices associated with the first image frame to threshold values, said threshold values being chosen so as to identify which matrix elements correspond to a $M_x$ by $M_y$ pixel block which includes pixel values potentially representing an image of the subject's pupil and at least the portion of the subject's iris; and tracking the location of a center of each $M_x$ by $M_y$ pixel block potentially representing the image of the subject's pupil and at least the portion of the subject's iris in each subsequent image frame produced from the imaging apparatus, and detecting a blink at the location, said blink indicating the location is an actual eye location.

13. The method of claim 12, wherein the tracking and blink detecting step comprises the step of:

(a) determining the center of the $M_x$ by $M_y$ pixel block which includes pixel values potentially representing the image of the subject's pupil and at least the portion of the subject's iris.

14. The method of claim 13, wherein the tracking and blink detecting step further comprises the steps of:

(b) selecting cut-out pixel blocks in a next consecutive image frame produced by the imaging apparatus, each of said cut-out pixel blocks respectively comprising a $M_x$ by $M_y$ pixel block corresponding to the location of a pixel block in a immediately preceding image frame which was identified as potentially representing the image of the subject's pupil and at least the portion of the subject's iris, as well as a number of pixels which surround the identified pixel block;

(c) respectively forming a matrix of intensity representing pixel values from an area surrounding the center of each $M_x$ by $M_y$ pixel block identified as potentially representing the image of the subject's pupil and at least the portion of the subject's iris in a last preceding image frame in which such a center was determined;

(d) correlating an appropriate one of the matrices formed in step (c) with each element of the associated cutout block, said correlation being performed by first sequentially overlaying the center element of said appropriate one of said matrices onto each pixel value of said associated cut-out block starting with the uppermost left-hand corner, and second, performing a correlation between the overlaid matrix and the cut-out block for each overlaid cut-out block pixel location, to create a matrix of correlation coefficients for each cut-out block in said next consecutive image frame;

(e) comparing a correlation threshold value to each element in each correlation coefficient matrix;

(f) flagging any correlation coefficient matrix element which exceeds said correlation threshold value in each of the correlation coefficient matrices;

(g) if elements of a correlation coefficient matrix are flagged in step (f), determining which flagged correlation coefficient element in the correlation coefficient matrix has the greatest value, wherein said element having the greatest value in the matrix corresponds to the center pixel value of the $M_x$ by $M_y$ pixel block which includes pixel values potentially representing the image of the subject's pupil and at least the portion of the subject's iris in said next consecutive image frame;

(h) if no elements of a correlation coefficient matrix are flagged in step (f), noting the lack of flagged elements condition in the matrix and calculating the number of consecutive times this condition has occurred; and (i) repeat steps (b) through (h) for each image frame produced by the imaging apparatus.

15. The method of claim 14, wherein each of said cut-out pixel blocks constitutes the $M_x$ by $M_y$ pixel block corresponding to the location of the pixel block in the immediately preceding image frame which was identified as potentially representing the image of the subject's pupil and at least the portion of the subject's iris, and all surrounding $M_x$ by $M_y$ pixel blocks which are adjacent to said pixel block.

16. The method of claim 14, wherein said area referred to in step (c) constitutes the $M_x$ by $M_y$ pixel block identified as potentially representing the image of the subject's pupil and at least the portion of the subject's iris in the last preceding image frame in which said center was determined, and all surrounding $M_x$ by $M_y$ pixel blocks which are adjacent to the identified pixel block.

17. The method of claim 14, wherein said threshold value is chosen so as to ensure a substantial degree of correlation between an overlaid matrix and an associated cut-out block.

18. The method of claim 14, wherein the tracking and blink detecting step further comprises the steps of:

(j) detecting that a blink has occurred in a location identified as potentially representing the image of the subject's pupil and at least the portion of the subject's iris whenever the number of consecutive times the lack of flagged elements condition calculated in step (h) for a correlation coefficient matrix associated with said location does not exceed about seven before elements of said correlation coefficient matrix are flagged in step (f);

(k) designating the center of the $M_x$ by $M_y$ pixel block corresponding said location where a blink has been detected in step (j) as an actual eye location.

19. The method of claim 18, further comprising the steps of:

assigning a low confidence status to a location identified as potentially representing the image of the subject's pupil and at least the portion of the subject's iris whenever the number of consecutive times the lack of flagged elements condition calculated in step (h) for a correlation coefficient matrix associated with said location exceeds 0.5, said low confidence status indication the location is not likely to be an actual eye; and assigning a low confidence status to a location identified as potentially representing the image of the subject's pupil and at least the portion of the subject's iris whenever a blink is not detected in step (j) at the location for 150 consecutive image frames.

20. The method of claim 19, further comprising the step of assigning a low confidence status to a location identified as an actual eye location in step (k) whenever the number of consecutive times the lack of flagged elements condition calculated in step (h) for a correlation coefficient matrix associated with said location exceeds 150 and there is no other location identified as an actual eye location within prescribed horizontal and vertical distance ranges from the actual eye location, said prescribed horizontal distance range having an upper limit corresponding to the maximum expected horizontal eye separation of the subject and a lower limit corresponding to the minimum expected horizontal eye separation of the subject, and said prescribed vertical distance range having an upper limit corresponding to the maximum expected vertical eye separation of the subject and a lower limit corresponding to the minimum expected vertical eye separation of the subject.

21. The method of claim 20, further comprising the step of reinitializing the system whenever all the locations identified as potentially representing the image of the subject's pupil and at least the portion of the subject's iris or actual eye locations are assigned a low confidence status.

22. An eye position finding and tracking system comprising:

an imaging apparatus which produces digital image frames including the face and eyes of a subject, each digital image frame comprising an array of pixel values representing the intensity of light reflected from the face of the subject, wherein each intensity representing pixel value is located at a position in the array specified by x and y coordinates; and a eye finding and tracking unit comprising:
a first processor portion capable of averaging the intensity representing pixel values within respective $M_x$ by $M_y$ pixel blocks of a digitized image frame to create elements of output matrices, a second processor portion capable of comparing elements of the output matrices to threshold values, said threshold values being chosen so as to identify which matrix elements correspond to a $M_x$ by $M_y$ pixel block which includes pixel values potentially representing an image of the subject's pupil and at least the portion of the subject's iris.

23. The system of claim 22, wherein said first processor portion comprises:

first means for respectively averaging the intensity representing pixel values within three vertically arranged $M_x$ by $M_y$ pixel blocks in the upper left-hand corner of said digitized image frame to create a first three-element column of an output matrix;

second means for respectively averaging the intensity representing pixel values within three vertically arranged $M_x$ by $M_y$ pixel blocks each of which is offset to the right by one column of the array in relation to a last averaged pixel block to create a new column of the output matrix; and first repeating means for repeatedly employing the first and second averaging means until three vertically arranged $M_x$ by $M_y$ pixel blocks which include pixel values from the last column of the array have been averaged to create a last column of the output matrix.

24. The system of claim 23, wherein said first processor portion further comprises:

third means for respectively averaging the intensity representing pixel values within three vertically arranged $M_x$ by $M_y$ pixel blocks starting at a position on the left-hand side of the array which is offset downward by one row in relation to a previously averaged pixel block to create a first three-element column of a new output matrix;

fourth means for respectively averaging the intensity representing pixel values within three vertically arranged $M_x$ by $M_y$ pixel blocks each of which is offset to the right by one column of the array in relation to a last averaged pixel block to create a new column of the new output matrix;

second repeating means for repeatedly employing the third and fourth averaging means until three vertically arranged $M_x$ by $M_y$ pixel blocks which include pixel values from the last column of the array have been averaged to create a last column of the new output matrix; and third repeating means for repeatedly employing the third and fourth averaging means and the second repeating means until three vertically arranged $M_x$ by $M_y$ pixel blocks which include pixel values from the last column and row of the array have been averaged to create a last column of a last new output matrix.

25. The system of claim 24, wherein said second processor portion comprises:

first means for comparing each element of each output matrix to a threshold range;

means for flagging any output matrix element which both exceeds a lower limit of the threshold range and is less than an upper limit of the threshold range;

second means for comparing a threshold value to the average of the intensity representing pixel values within each $M_x$ by $M_y$ pixel block immediately surrounding any pixel block corresponding to an output matrix element flagged by the flagging means.

26. The system of claim 25, wherein said threshold range comprises:

a lower limit representing the lowest expected average of the intensity representing pixel values within a $M_x$ by $M_y$ pixel block corresponding to an image of the subject's pupil and at least a portion of the subject's iris for the particular illumination condition present at the time the image was produced; and an upper limit representing the highest expected average of the intensity representing pixel values within the $M_x$ by $M_y$ pixel block corresponding to the image of the subject's pupil and at least the portion of the subject's iris for the particular illumination condition present at the time the image was produced.

27. The system of claim 25, wherein the same threshold value is compared to the average of the intensity representing pixel values associated with each $M_x$ by $M_y$ pixel block immediately surrounding any pixel block corresponding to a flagged output matrix element, and wherein said threshold value comprises a lowest expected average of the intensity representing pixel values within any $M_x$ by $M_y$ pixel block immediately surrounding a $M_x$ by $M_y$ pixel block corresponding to an image of the subject's pupil and at least a portion of the subject's iris for the particular illumination condition present at the time the image was produced, and wherein the second processor portion further comprises means for de-flagging any previously flagged output matrix element which has any surrounding pixel block which fails to exceed the threshold value.

28. The system of claim 27, wherein said eye finding and tracking unit further comprises a third processor portion comprising:

means for identifying groups of flagged matrix elements having any common intensity representing pixel values associated with the respective $M_x$ by $M_y$ pixel blocks corresponding to the flagged matrix elements;

means for determining one of (1) which of the flagged matrix elements in each of said groups are greater than the others, or (2) whenever no one element has the greatest value, which of the flagged matrix elements in each of said groups is in the geometric center of the group; and second means for deflagging any of the flagged matrix elements identified by the identifying means which were not determined to be greater or in the center by the determining means.

29. The system of claim 28, wherein said eye finding and tracking unit further comprises a fourth processor portion capable of determining if a $M_x$ by $M_y$ pixel block corresponding to a flagged matrix element is within prescribed horizontal and vertical distance ranges from a $M_x$ by $M_y$ pixel block corresponding to another flagged matrix element, said prescribed horizontal distance range having an upper limit corresponding to the maximum expected horizontal eye separation of the subject and a lower limit corresponding to the minimum expected horizontal eye separation of the subject, and said prescribed vertical distance range having an upper limit corresponding to the maximum expected vertical eye separation of the subject and a lower limit corresponding to the minimum expected vertical eye separation of the subject.

30. The system of claim 25, wherein a different threshold value is compared to the average of the intensity representing pixel values associated with each $M_x$ by $M_y$ pixel block immediately surrounding any pixel block corresponding to a flagged output matrix element, and wherein the respective threshold value comprises a lowest expected average of the intensity representing pixel values within the associated $M_x$ by $M_y$ pixel block immediately surrounding a central $M_x$ by $M_y$ pixel block corresponding to an image of the subject's pupil and at least a portion of the subject's iris for the particular illumination condition present at the time the image was produced in immediately surrounding pixel blocks which exhibit an average intensity exceeding that of an average intensity of said digitized image frame, and a highest expected average of the intensity representing pixel values within the associated $M_x$ by $M_y$ pixel block immediately surrounding the central $M_x$ by $M_y$ pixel block corresponding to the image of the subject's pupil and at least a portion of the subject's iris for the particular illumination condition present at the time the image was produced in immediately surrounding pixel blocks which exhibit an average intensity less than that of the average intensity of said digitized image frame, and wherein the second processor portion further comprises means for de-flagging any previously flagged output matrix element which has any surrounding pixel block which either (1) fails to exceed the threshold value in the immediately surrounding pixel blocks which exhibit an average intensity exceeding that of an average intensity of said digitized image frame, or (2) fails to be less than the threshold value produced in the immediately surrounding pixel blocks which exhibit an average intensity less than that of the average intensity of said digitized image frame.

31. The system of claim 30, wherein said eye finding and tracking unit further comprises a third processor portion comprising:
means for identifying groups of flagged matrix elements having any common intensity representing pixel values associated with the respective $M_x$ by $M_y$ pixel blocks corresponding to the flagged matrix elements;
means for determining one of (1) which of the flagged matrix elements in each of said groups are greater than the others, or (2) whenever no one element has the greatest value, which of the flagged matrix elements in each of said groups is in the geometric center of the group; and
second means for deflagging any of the flagged matrix elements identified by the identifying means which were not determined to be greater or in the center by the determining means.

32. The system of claim 31, wherein said eye finding and tracking unit further comprises a fourth processor portion capable of determining if a $M_x$ by $M_y$ pixel block corresponding to a flagged matrix element is within prescribed horizontal and vertical distance ranges from a $M_x$ by $M_y$ pixel block corresponding to another flagged matrix element, said prescribed horizontal distance range having an upper limit corresponding to the maximum expected horizontal eye separation of the subject and a lower limit corresponding to the minimum expected horizontal eye separation of the subject, and said prescribed vertical distance range having an upper limit corresponding to the maximum expected vertical eye separation of the subject and a lower limit corresponding to the minimum expected vertical eye separation of the subject.

33. An eye position finding and tracking system comprising:
an imaging apparatus which produces digital image frames including the face and eyes of a subject, each digital image frame comprising an array of pixel values representing the intensity of light reflected from the face of the subject, wherein each intensity representing pixel value is located at a position in the array specified by x and y coordinates; and
a eye finding and tracking unit comprising:
a first processor portion capable of averaging the intensity representing pixel values within respective $M_x$ by $M_y$ pixel blocks of a first digitized image frame to create elements of output matrices,
a second processor portion capable of comparing elements of the output matrices associated with the first image frame to threshold values, said threshold values being chosen so as to identify which matrix elements correspond to a $M_x$ by $M_y$ pixel block which includes pixel values potentially representing an image of the subject's pupil and at least the portion of the subject's iris,
a third processor portion capable of tracking the location of a center of each $M_x$ by $M_y$ pixel block potentially representing the image of the subject's pupil and at least the portion of the subject's iris in each subsequent image frame produced from the imaging apparatus, and detecting a blink at the location, said blink indicating the location is an actual eye location.

34. The system of claim 33, wherein the third processor portion comprises first determining means for determining the center of the $M_x$ by $M_y$ pixel block which includes pixel values potentially representing the image of the subject's pupil and at least the portion of the subject's iris.

35. The system of claim 34, wherein the third processor portion further comprises:
means for selecting cut-out pixel blocks in a next consecutive image frame produced by the imaging apparatus, each of said cut-out pixel blocks respectively comprising a $M_x$ by $M_y$ pixel block corresponding to the location of a pixel block in a immediately preceding image frame which was identified as potentially representing the image of the subject's pupil and at least the portion of the subject's iris, as well as a number of pixels which surround the identified pixel block;
means for respectively forming a matrix of intensity representing pixel values from an area surrounding the center of each $M_x$ by $M_y$ pixel block identified as potentially representing the image of the subject's pupil and at least the portion of the subject's iris in a last preceding image frame in which such a center was determined;

means for correlating an appropriate one of the matrices formed by the forming means with each element of the associated cutout block, said correlation being performed by first sequentially overlaying the center element of said appropriate one of said matrices onto each pixel value of said associated cut-out block starting with the uppermost left-hand corner, and second, performing a correlation between the overlaid matrix and the cut-out block for each overlaid cut-out block pixel location, to create a matrix of correlation coefficients for each cut-out block in said next consecutive image frame;

means for comparing a correlation threshold value to each element in each correlation coefficient matrix;

means for flagging any correlation coefficient matrix element which exceeds said correlation threshold value in each of the correlation coefficient matrices;

second determining means for determining which flagged correlation coefficient element in the correlation coefficient matrix has the greatest value whenever elements of a correlation coefficient matrix are flagged by the flagging means, wherein said element having the greatest value in the matrix corresponds to the center pixel value of the $M_x$ by $M_y$ pixel block which includes pixel values potentially representing the image of the subject's pupil and at least the portion of the subject's iris in said next consecutive image frame;

means for noting the lack of flagged elements condition in the matrix and calculating the number of consecutive times this condition has occurred whenever no elements of a correlation coefficient matrix are flagged by the flagging means; and means for repeatedly employing the selecting, forming, correlating, comparing flagging second determining, and noting means for each image frame produced by the imaging apparatus.

36. The system of claim 35, wherein each of said cut-out pixel blocks constitutes the $M_x$ by $M_y$ pixel block corresponding to the location of the pixel block in the immediately preceding image frame which was identified as potentially representing the image of the subject's pupil and at least the portion of the subject's iris, and all surrounding $M_x$ by $M_y$ pixel blocks which are adjacent to said pixel block.

37. The system of claim 35, wherein said area surrounding the center of each $M_x$ by $M_y$ pixel block identified as potentially representing the image of the subject's pupil and at least the portion of the subject's iris in the last preceding image frame in which such a center was determined constitutes the $M_x$ by $M_y$ pixel block identified as potentially representing the image of the subject's pupil and at least the portion of the subject's iris in the last preceding image frame in which said center was determined, and all surrounding $M_x$ by $M_y$ pixel blocks which are adjacent to the identified pixel block.

38. The system of claim 35, wherein said threshold value is chosen so as to ensure a substantial degree of correlation between an overlaid matrix and an associated cut-out block.

39. The system of claim 35, wherein the third processor portion further comprises:

means for detecting that a blink has occurred in a location identified as potentially representing the image of the subject's pupil and at least the portion of the subject's iris whenever the number of consecutive times the lack of flagged elements condition calculated by the noting means for a correlation coefficient matrix associated with said location does not exceed about seven before elements of said correlation coefficient matrix are flagged by the flagging means;

means for designating the center of the $M_x$ by $M_y$ pixel block corresponding said location where a blink has been detected by the detecting means as an actual eye location.

40. The system of claim 39, further comprising a fourth processor portion, said fourth processor portion comprising:

first means for assigning a low confidence status to a location identified as potentially representing the image of the subject's pupil and at least the portion of the subject's iris whenever the number of consecutive times the lack of flagged elements condition calculated by the noting means for a correlation coefficient matrix associated with said location exceeds 150, said low confidence status indication the location is not likely to be an actual eye; and second means for assigning a low confidence status to a location identified as potentially representing the image of the subject's pupil and at least the portion of the subject's iris whenever a blink is not detected by the detecting means at the location for 150 consecutive image frames.

41. The system of claim 40, wherein the fourth processor portion further comprises third means for assigning a low confidence status to a location identified as an actual eye location by the designating means whenever the number of consecutive times the lack of flagged elements condition calculated by the noting means for a correlation coefficient matrix associated with said location exceeds 150 and there is no other location identified as an actual eye location within prescribed horizontal and vertical distance ranges from the actual eye location, said prescribed horizontal distance range having an upper limit corresponding to the maximum expected horizontal eye separation of the subject and a lower limit corresponding to the minimum expected horizontal eye separation of the subject, and said prescribed vertical distance range having an upper limit corresponding to the maximum expected vertical eye separation of the subject and a lower limit corresponding to the minimum expected vertical eye separation of the subject.

42. The system of claim 41, wherein the fourth processor portion further comprises means for reinitializing the system whenever all the locations identified as (i) potentially representing the image of the subject's pupil and at least the portion of the subject's iris and (ii) actual eye locations are assigned a low confidence status.

* * * * *